United States Patent [19]

Conte et al.

[11] Patent Number: 5,681,583
[45] Date of Patent: Oct. 28, 1997

[54] MULTILAYERED CONTROLLED-RELEASE ORAL SOLID PHARMACEUTICAL FORMS

[75] Inventors: Ubaldo Conte; Lauretta Maggi; Paolo Giunchedi, all of Pavia, Italy

[73] Assignee: APR Applied Pharma Research SA, Stabio, Switzerland

[21] Appl. No.: 397,187

[22] PCT Filed: Apr. 2, 1994

[86] PCT No.: PCT/EP94/01050

§ 371 Date: Apr. 25, 1995

§ 102(e) Date: Apr. 25, 1995

[87] PCT Pub. No.: WO95/01781

PCT Pub. Date: Jan. 19, 1995

[30] Foreign Application Priority Data

Jul. 9, 1993 [IT] Italy ................. MI93A1486

[51] Int. Cl.$^6$ ..................................... A61K 9/24
[52] U.S. Cl. ............. 424/472; 424/466; 424/468; 424/473
[58] Field of Search ................ 424/472, 473, 424/466, 468

[56] References Cited

U.S. PATENT DOCUMENTS

| | | |
|---|---|---|
| 2,887,438 | 9/1959 | Cooper et al. ............... 167/82 |
| 2,951,792 | 9/1960 | Swintosky ................... 167/82 |
| 2,993,836 | 7/1961 | Nash et al. .................. 167/82 |
| 4,786,503 | 11/1988 | Edgren et al. .............. 424/443 |

FOREIGN PATENT DOCUMENTS

| | | |
|---|---|---|
| 0 384 514 | 8/1990 | European Pat. Off. . |
| 0598309A2 | 5/1994 | European Pat. Off. . |
| 93424 | 11/1909 | Israel . |
| 65328 | 3/1982 | Israel . |
| 2 123 291 | 2/1984 | United Kingdom . |
| 2 230 185 | 10/1990 | United Kingdom . |
| WO 88/08299 | 11/1988 | WIPO . |
| WO 93/05769 | 4/1993 | WIPO . |

*Primary Examiner*—Thurman K. Page
*Assistant Examiner*—James M. Spear
*Attorney, Agent, or Firm*—Nixon & Vanderhye

[57] ABSTRACT

Multilayered controlled-release solid pharmaceutical composition in tablet form suitable for oral administration comprising at least two layers containing active material in association with excipients and additives. One layer of the tablet releases a portion of the drug quickly while the other layer and optionally further layers release portions of the drug more gradually.

26 Claims, 5 Drawing Sheets

FIG. 6

MULTILAYERED CONTROLLED-RELEASE ORAL SOLID PHARMACEUTICAL FORMS

This application is a 35USC371 of PCT/EP94/01050 filed Apr. 2, 1994.

BACKGROUND OF THE INVENTION

The present invention relates to novel pharmaceutical forms for oral administration capable of releasing active substances at controlled and differentiated rate. It is well known that the pharmaceutical forms for the oral administration are the overwhelming majority of the pharmaceutical market for numerous and diversified reasons which, in the case of tablets, are mainly determined in that they guarantee precise dosage, excellent stability of carried active materials and easy administration. In the last twenty years, of great importance has been the achievement of more and more sophisticated and diversified pharmaceutical forms, with the purpose of simplifying the posological scheme and obtaining greater patient's compliance. Such so called modified or controlled release pharmaceutical forms were aimed at, in the majority of cases, releasing the active material carried therein at constant rate in time, following a release kinetics defined as being of zero order.

In some cases it was also possible to highlight that, to a drug release at a constant "in vitro" rate, corresponded a more regular trend of plasmatic levels obtainable consequently to the administration to the patient.

If, in theory, such approach could have been correct so far as some drugs are concerned, in practice it has been noticed that, in many cases, the pharmacokinetics and pharmacodynamics of the active material in biological liquids are influenced and sometimes strictly determined by chronobiological rhythms. Furthermore, the developments of systems able to release the active material at constant rate has brought about the designing and therapeutical utilization of dosage forms more and more sophisticated that required the use of always new polymeric substances with specific properties from the technological and productive point of view. However, such polymeric materials, which are normally biocompatible are, not always biodegradable as well, and this implies that residues of these polymeric materials employed in creating grid therapeutic systems could remain in the organism and, above all, by repeated administration, cause unwanted accumulation phenomena.

In this respect, the setting in of now and then serious and, in some cases, lethal side effects occurred following the administration of the so called OROS system osmotic pump disclosed in the U.S. Pat. No. 4,160,020, 1979.

In the majority of cases, the slowing down of the active material release is obtained by utilizing gellable hydrophilic polymers capable of swelling in contact with water and/or aqueous fluids, thereby forming a gelled layer. From these systems the active material is in general released according to Fickiam type kinetics. A number of studies and research work have been carried out in the past and also recently aiming at the modulation of the release rate of active principles. This research was originated for therapeutic reasons (for instance the achievement of determined hematic and bioavailability levels of the drug) and because of practical problems related to the timing of the drug administration. Generally these studies to proposals consisting in two layer tablets, prevailingly of concentric type, and capable of a fast release of the active principle whereas the other was formulated so as to provide a slow or delayed releasing of the drug.

In some cases (WO-A-9305769 and EP-A-0384514) the outer layer is that with slow release, whereas the inner one (thus accessible only when the outer layer has fulfilled its function) is of the fast release type.

In other cases (U.S. Pat. No. 2,993,836 and U.S. Pat. No. 2,887,438) the delayed release layer forms the core of the tablet, whereas the outer coating layer is formulated for a fast or instantaneous release of a portion of the active principle.

According to further proposals two layer tablets have been disclosed in which the composition of the slow release layer was taken into consideration.

For instance in U.S. Pat. No. 2,951,792 the slow release layer consists of lipidic matrix formed by fatty alcohols or acids or more generally fatty derivatives. Besides the features relating to the formulation, particular attention is paid to the tablet size and to the extension of the area from which the release takes place.

In the two layer tablet disclosed in GB-A-2123291, the fast release part has a conventional composition, whereas that with slow release must contain at least one surface active ingredient.

Moreover the release delaying agent consists of a mixture of cellulose derivatives and of a slow solubilizing agent for the polymer mixture (particularly PEG). EP-A-63266 discloses a two layer composition (a fast release and a slow release layer) wherein exclusively sodium alginate is used as the release delaying agent. However the prior proposals were not satisfactory for several reasons, whereby it is still of interest the problem of the therapeutical cases wherein the administration (as acute or symptomatic treatment) of a first therapeutically effective dose of an active material is required, whereas in a following step the slow or at a lower rate administration of a maintenance dose of the same or different drug is necessary. These therapeutic needs obviously require complicated posological schemes that are not always correctly adhered to by the patient, especially if outpatient subjects are involved; it is well known in fact that non-compliance with posological schemes is directly proportional to the complexity and number of the daily required of recommended administrations.

In the case, for example, of rheumatic diseases, particularly for the night time pain treatment, it would be better to have the availability of pharmaceutical forms capable of a fast release of a dose of the drug for the so called acute treatment, whilst a second quantity should be slowly released, in order to maintain for a more prolonged period of time a plasmatic level sufficiently high and therapeutically effective. That is, during this second step the release of the active substance should occur at a rate comparable to that of the drug elimination (due to either the metabolism or normal biological elimination processes).

BRIEF DESCRIPTION OF THE INVENTION

The main object of the present invention is to solve the above explained problems and drawbacks, keeping unchanged the oral administration form by means of tablets. A more specific object of the present invention is a novel pharmaceutical form containing one or more active substances that can be released with different release kinetics and, namely, that such pharmaceutical form be designed and realized to meet the specific therapeutic requirements of particular pathological situations as those quoted in the introduction. The new form is in fact intended mainly of the administration of one or more drugs, one of which must act immediately, while a hematic level or a therapeutic activity for a more prolonged period of time is required for the second active substance (or for a portion of the same active substance).

These objects are achieved with the pharmaceutical form of the invention, which consists of a solid form having at least two layers of which:

at least a first layer contains an active material, carried with usual excipients and additives, that are able to promote the compressibility of the mass, in which the active material is distributed, such as to guarantee an immediate release of the active material, and at least a second layer, superimposed upon the first one which, carries a portion of the same active material of said first layer or a second active material, the formulation of said second layer involving the use of excipients and adjuvants which can adjust the releasing rate of the active material at a definitely differentiated rate in comparison with that of the above mentioned first layer.

The novel formulation in accordance with the present invention allows, the use of well-established production technologies and to obtain the possibility of administering one or more active materials that are released by the pharmaceutical formulation with differentiated releasing rates.

The designed and realised system, as better pointed out by the examples supporting the present application, is intended for the administration of:

1- One drug only, released at different rates: one quantity immediately and a quantity within a prolonged and/or programmable period of time.

2- Two drugs, one of which is immediately released and the second one within a more prolonged period of time.

3- Association of two drugs, of which one quantity (drug 1+drug 2) is immediately released and one quantity (of both) over a prolonged period of time.

4- Three drugs, one of which is released fast, a second one which is released at a "in vitro" programmable speed in a longer period of time, and a the third one, that is released in an even more prolonged period of time.

BRIEF DESCRIPTION OF THE DRAWINGS

The invention will now be described in more detail with reference to the accompanying drawings, in which.

DETAILED DESCRIPTION OF PREFERRED EMBODIMENTS

In preparing the different layers, besides the active material and depending on its solubility characteristics in water and/or aqueous liquids, polymeric materials capable of adjusting (slow down and/or accelerate) the active material release are also employed.

Among these substances of particular importance as regards the release rate are the so-called disintegrating and superdisintegrating polymers. Exhaustive information about these polymers are contained in the paper by Shangrow R, et el. Pharmaceutical Technology, October 1980, which is, incorporated herein by reference.

With regard to active materials sparingly soluble in water, particular adjuvants to facilitate a rapid solubilization can be used, such as cyclodextrins, superdisintegrators, etc., as reported in the book "Techniques of solubilization of drugs" by S. H. Yalkowsky Ed. M. Dekker, New York 1985, and in the Italian patent application No. 21091 A/90 of Jul. 20, 1990.

Active materials for the prevention of anginous attacks and hypertensive attacks, such as:

trapidil, diltiazem, verapamil, urapidil, or anti-inflammatory non steroidal (NSAID) or steroidal drugs: trapidil (7-diethylamino-5-methyl-1,2,4-triazol[1,5-a] pyrimidine), diltiazem hydrochloride (cis-(+)-3-acetoxy-5-(2-dimethylaminoethyl)-2,3-dihydro-2-(4-methoxyphenyl)-1,5-benz othiazepin-4(5H)-one hydrochloride), verapamil hydrochloride (5-[N-(3,4-dimetheoxyphenethyl)-N-methylamino]-2-(3,4-dimethoxyphenyl)-2-isopropylv aleronitrile hydrochloride), Urapidil hydrochloride (6-[3-(4-o-methoxyphenylpiperazin-1-yl)propylamino]-1,3-dimethylpyrimidine-2,4(1H,3H)-dione hydrochloride)or non steroidal antiinflammatory drugs (NSSAID) or steroidal diclofenac sodium (sodium 2-(2,6-dichloroanilino)phenyl] acetate), indomethacin ([1-(4-chlorobenzoyl)-5-methoxy-2-methylindol-3-yl]acetic acid), ibuprofen lysine salt (2-(4-isobutylphenyl)propionic acid compounded with L-2,6-diaminohexanoic acid acetate), ketoprofen (2-(3-benzoylphenyl)propionic acid), diflusinal (–(2,4-difluorophenyl)salicylic acid), piroxicam (4-hydroxy-2-methyl-N-(2-pyridyl)-2H-1,2-benzothiazine-3-caboxamide 1,1-dioxide), naproxen (+)-2-(6-methoxy-2-naphtyl) propionic acid), flurbiprofen (2-(2-fluorobiphenyl-4-yl) propionic acid) or sleeping substances and tranquillizers, such as diazepam (7-chloro-1,3-dihydro-1-methyl-5-phenyl-2H-1,4-benzodiazepin-2-one), nitrazepam (1,3-dihydro-7-nistro-5-phenyl-1,4-benzodiazepin-2-one) or antihistaminic and/or antiasthmatic drugs, such as ephedrine ((1R,2S)-2-methylamino-1-phenylpropan-1-ol hemihydrate), terfenadine (1-(4-tert-butylphenyl)-4-[4-(α-hydroxybenzhydryl)piperidino]butan-1-ol), teophhylline (3,7-dihydro-1,3-dimethylpurine-2,6(1H)-dione), chlorpheniramine ((±)-3-(4-chloro-phenyl)-NN-dimethyl-3-(2-pyridyl)propylamine hydrogen maleate) can be carried in the described pharmaceutical form.

As polymeric substances for the preparation of said for fast release layer of the active material, cross-linked polyvinylpyrrolidone, microcrystalline cellulose and cellulose derivatives, cross-linked sodium carboxymethylcellulose, carboxymethylstarch, potassium methacrylate-divinylbenzene copolymer, polyvinylalcohols, starches, starch derivatives, beta cyclodextrin and dextrin derivatives in general may be for example employed. Said polymeric substances make up from 10% to 90% of the layer's weight.

In said first layer other adjuvant substances may further find utilization, consisting of the so called effervescent mixtures, namely that can rapidly disintegrate the tablet or, in the specific case, the layer when it comes in contact with aqueous liquids and, preferably, with gastric juice.

These substances include the carbonates and bicarbonates of sodium and of other alkali metals or earth-alkali metals, the glycine sodium carbonate and other pharmaceutically acceptable salts, capable of producing effervescence in an acid environment.

Depending on the pH of the medium where the rapid disintegration of the compacted product should occur, further substances such as citric, tartaric, fumaric acids that can produce the effervescence and the rapid disintegration of the compacted product may find use in the formulation.

In the preparation of the slow release second layer, adjuvants may be used such as natural and/or synthetic polymeric materials belonging to the class of the so called hydrophilic gellable polymers, capable of slowing down the active material release from said layer.

The polymeric materials for the preparation of the slow release second layer may be selected in the class that includes hydroxypropylmethylcellulose of a molecular weight of between 1,000 and 4,000,000, hydroxypropylcellulose of a molecular weight of between from 2,000 to 2,000,000, carboxyvinylpolymers, polyvinyl alcohols, glucans, scleroglucans, mannans, xanthans, carboxymethylcellulose and its derivatives, methylcellulose and, in general, cellulose derivatives.

Of all the mentioned polymers various types are commercially available, characterized by different chemical, physical, solubility and gelling properties, in particular concerning hydroxypropylmethylcellulose, various types of different molecular weight (1,000 to 4,000,000) and different substitution degree can be employed.

Said hydroxypropylmethylcellulose types exhibit different characteristics, being prevailingly erodible or prevailingly gellable as a function of the viscosity in the polymeric chain. According to the solubility of the active material and of the hydration and/or erosion properties of the polymeric substance, different release and "in vitro" programmable rates could be achieved by suitable tests.

Said polymeric substances might be present in a percentage of 5 to 90% based on the total weight of said second layer but, preferably, from 50 to 85%.

Finally, excipients usually employed in the pharmaceutical technics can find application, such as mannitol, lactose, magnesium stearate, colloidal silica and others like glyceril monostearate, hydrogenated castor oil, waxes, mono-, bi- and tri-substituted glycerides.

Onto said finished tablets, a film of polymeric gastroresistant and enterosoluble material may be further applied, in order to allow the activation of the system only after the tablet has reached the duodenal-intestinal tract.

Pharmaceutical systems of this latter type might find use to make tablets specifically designed and intended to release the active material in the last part of the intestinal tract, namely at the colon level.

Cellulose acetophthalate, cellulose acetopropionate, cellulose trimellitate, acrylic and methacrylic polymers and copolymers, having different molecular weight and solubility depending on different pH values, may be used as polymeric materials for realizing gastroresistant systems.

Said gastroresistant and enterosoluble materials can be also utilized associated with retardant polymers.

Said gastroresistant and enterosoluble materials can be also utilized in combination with retardant polymers.

The pharmaceutical forms of the present invention allow therapeutic results and quite impredictable advantages to be reached as will be confirmed by experimental tests carried out both "in vitro" and "in vivo".

Referring for sake of description simplicity to the case wherein only one active material is administered either in the immediate release form or in that of programmed release, the pharmaceutical form of the present invention is likely to achieve the following results:

1) The immediate release of an amount of active material such as to set a plasmatic concentration equal to the minimum threshold needed for a symptomatic or active treatment; If, in the pharmaceutical forms for oral use with immediate release, a peak or maximum is reached in a time relatively closed to the administration arriving at a plasmatic concentration greater than the minimum required for a symptomatic therapeutic effect, this also means that with the new pharmaceutical form of the present invention the administered dosage is lower as compared to that usually estimated for the acute treatment.

Considering also that many of the drugs involved in the present invention, as for example the anti-inflammatory active principles, often exhibit high toxicity and are gastro-detrimental the important advantage thus achieved is clearly evident.

The slow or retarded release of the same active material starts when a plasmatic concentration, higher than that which can be achieved with the only slow release form is already secured, whereby higher plasma levels are obtained than those which can be achieved with only the slow release form, the time being the same from the beginning of the treatment.

Another aspect adds to such therapeutically important results, namely that the pharmaceutical form of the present invention is prepared by means of production technologies consolidated in the practice and presently used, whereby are directly applicable on industrial scale.

EXAMPLES

The following examples describe, by way of illustration and by no limitation whatsoever, the preparation of the pharmaceutical forms according to the invention.

Example 1

Two-layered tablet, containing 200 mg trapidil, one layer of which contains 50 mg for a fast release and the second slow release layer with additional 150 mg trapidil.

1-a Preparation of the granulate forming the first fast release layer, comprising as active material 50 mg trapidil.

| | |
|---|---|
| Trapidil (B.15910100) | 50.0 mg |
| Lactose (C. Erba, Milan, I) | 25.0 mg |
| Starch maize (C. Erba, Milan, I) | 15.0 mg |
| Polyvinylpyrrolidone (Plasdone K29–32, Gaf Corp., Wayne, NY USA) | 1.0 mg |
| Carboxymethylstarch (Explotab, Edward Mendell Co. Inc. Carmel, NY USA) | 10.0 mg |
| Magnesium stearate (C. Erba, Milan, I) | 2.0 mg |
| Talc (C. Erba, Milan, I) | 3.0 mg |
| Total | 106.0 mg |

Trapidil, lactose and maize starch are mixed and wetted with a 10% polyvinylpyrrolidone solution in ethanol, followed by sieving on a 25 mesh sieve, drying so produced the granulate in an oven up to constant weight and sieving again on the same sieve. Carboxymethyl starch, magnesium stearate and talc are added, mixing thereafter in Turbula for 15 minutes.

A granulate (granulate A) is in this way made, showing good flow and compacting properties. The granulate undergoes the compression step as hereinafter described.

1-b Preparation of the granulate used to prepare the second layer containing 150 mg slow release trapidil

| | |
|---|---|
| Trapidil (B.15910100) | 150.0 mg |
| Mannitol (C. Erba, Milan, I) | 85.0 mg |

7

-continued

| | |
|---|---|
| Hydroxypropylmethylcellulose (Methocel K 4 M, Colocorn Orpinton UK) | 45.0 mg |
| Polyvinylpyrrolidone (Plasdone K29-32, Gaf Corp., Wayne, NY, USA) | 7.5 mg |
| Magnesium stearate (C. Erba, Milan, I) | 1.5 mg |
| Colloidal silica (Syloid 244, Grace GmbH, Worms D) | 1.5 mg |
| Total | 290.5 mg |

Trapidil, mannitol and hydroxypropylmethylcellulose are mixed and wetted with a 10% ethanol solution of pyrrolidone.

After sieving on a 25 mesh sieve, so produced the granulate is dried in an oven at 40° C. up to constant weight and sieved again on the same sieve. The magnesium stearate and colloidal silice are added and mixed in Turbula for 10 minutes. With this procedure a granulate (granulate B) is obtained with good flow and compacting properties. The granulate undergoes the compression step as hereinafter described.

1-c Preparation of finished systems (by compression)

Figure 1:
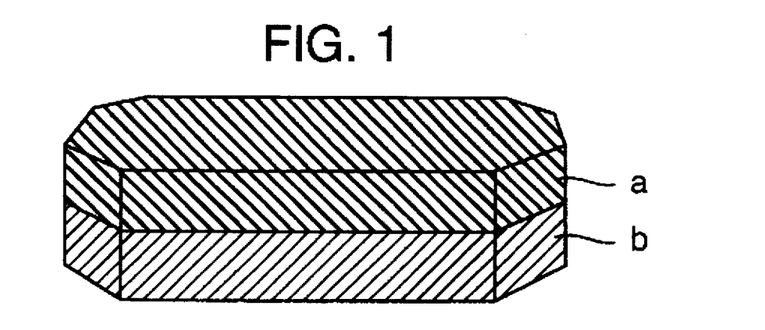
FIG. 1 shows an embodiment of the invention with two layers a and b.
Figure 2:
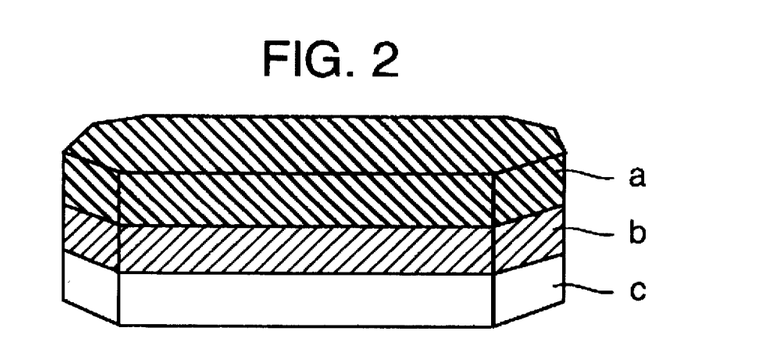
FIG. 2 shows an embodiment with three layers a, b and c.

A Layer Press rotative compression machine (Manesty Liverpool U.K.) is, used to prepare tablets as shown in FIG. 1b; this machine as known by those skilled in the art, consist of a rotative compression mechanism equipped with two or three loading stations and thus able to make two or three layered tablets. In the specific case, the machine is assembled and set to produce two layered tablets. The machine for this purpose is equipped with oblong (capsule-type) punches of 16×16 min. The first loading hopper is filled with the granulate described at point 1-a (granulate A), while the second one is filled with the granulate described at point 1-b (granulate B). The First loading station is adjusted so as to provide layers of 106 mg granulate (equal to 50 mg active material) while the second loading station is adjusted so as to provide an amount of granulate B (slow release active material) of 290,5 mg equal to 150 mg active material.

By operating as previously illustrated, two-layered tablets, are produced weighing on average 396.5 mg which totally contain 200 mg trapidil. Said finished systems are subjected to the dissolution test as hereunder specified.

1-d Dissolution test

To evaluate the releasing features of the finished (two-layered) systems, the basket apparatus 1 (described in USP XXII) is utilized, operating at 100 r.p.m. and using as a dissolution fluid 1000 ml of deionized water at 37° C. The active material release is monitored by U.V. spectrophotometric determination at 299 nm, with an automatic system of sampling and quantitative determination, and with an automatic data processing program(Spectrocomp 602, Advanced Products-Milano) The test results are listed in Table 1

TABLE 1

| Time (min) | % released trapidil |
|---|---|
| 15 | 27,0 |
| 30 | 37,5 |
| 60 | 45,3 |
| 120 | 57,7 |
| 240 | 75,5 |
| 360 | 100,6 |

It clearly appears that 25% of the 200 mg of the carried active material (first amount) is fast released in 15 minutes, whereas the second amount is released in about 6 hrs.

8

Figure 3:
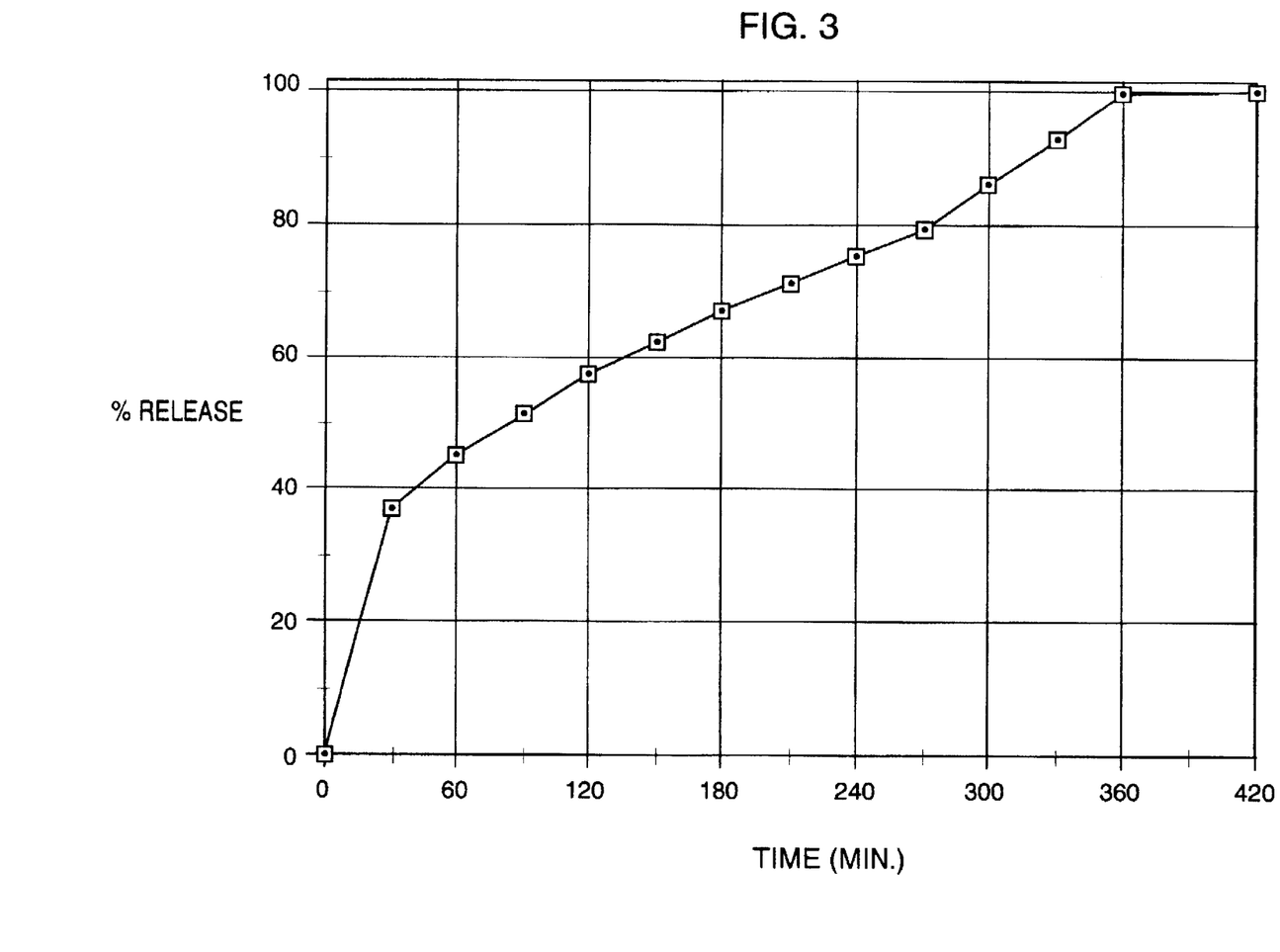
FIGS. 3–5 are graphs showing percentage release profiles.
Figure 4:
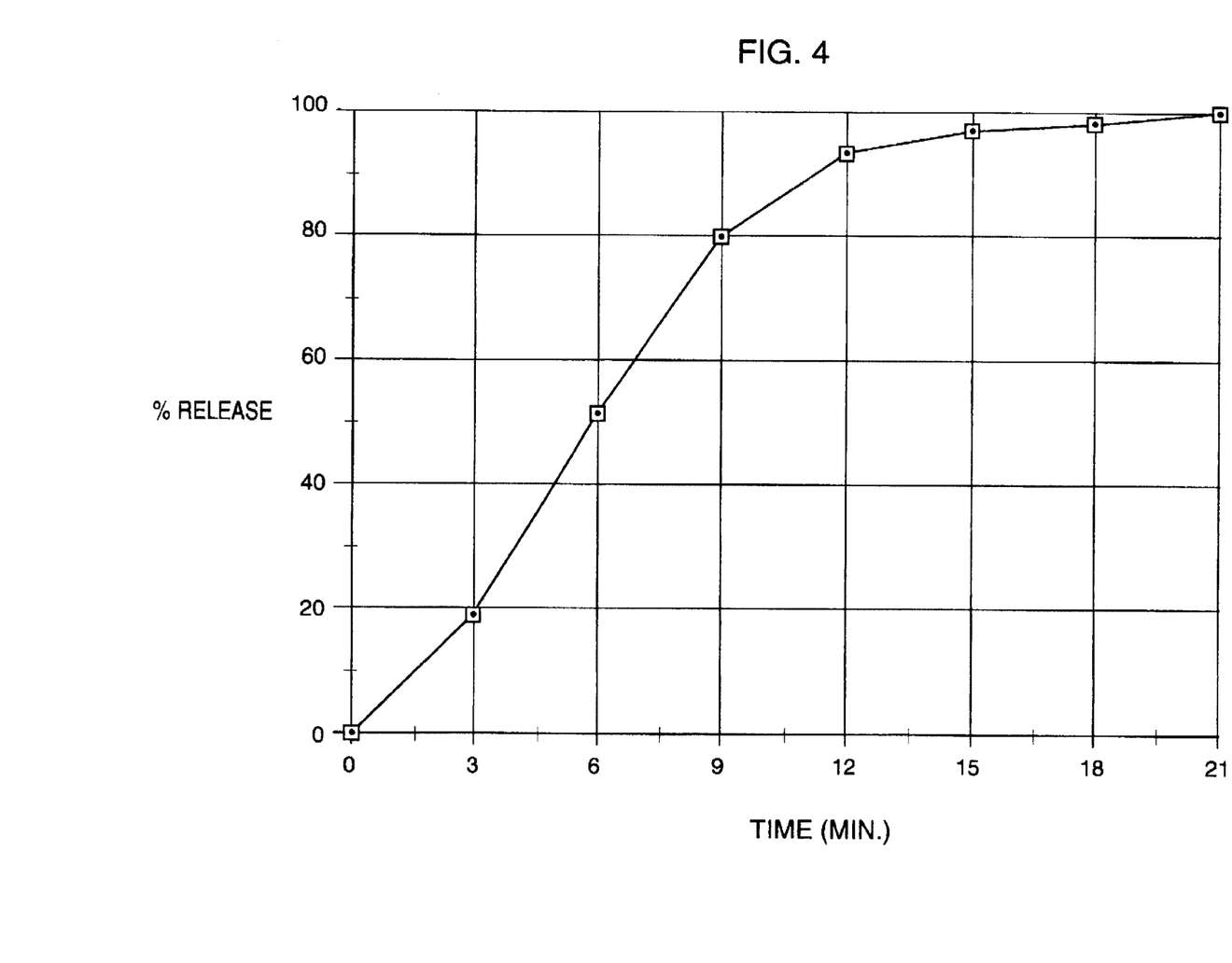
Figure 5:
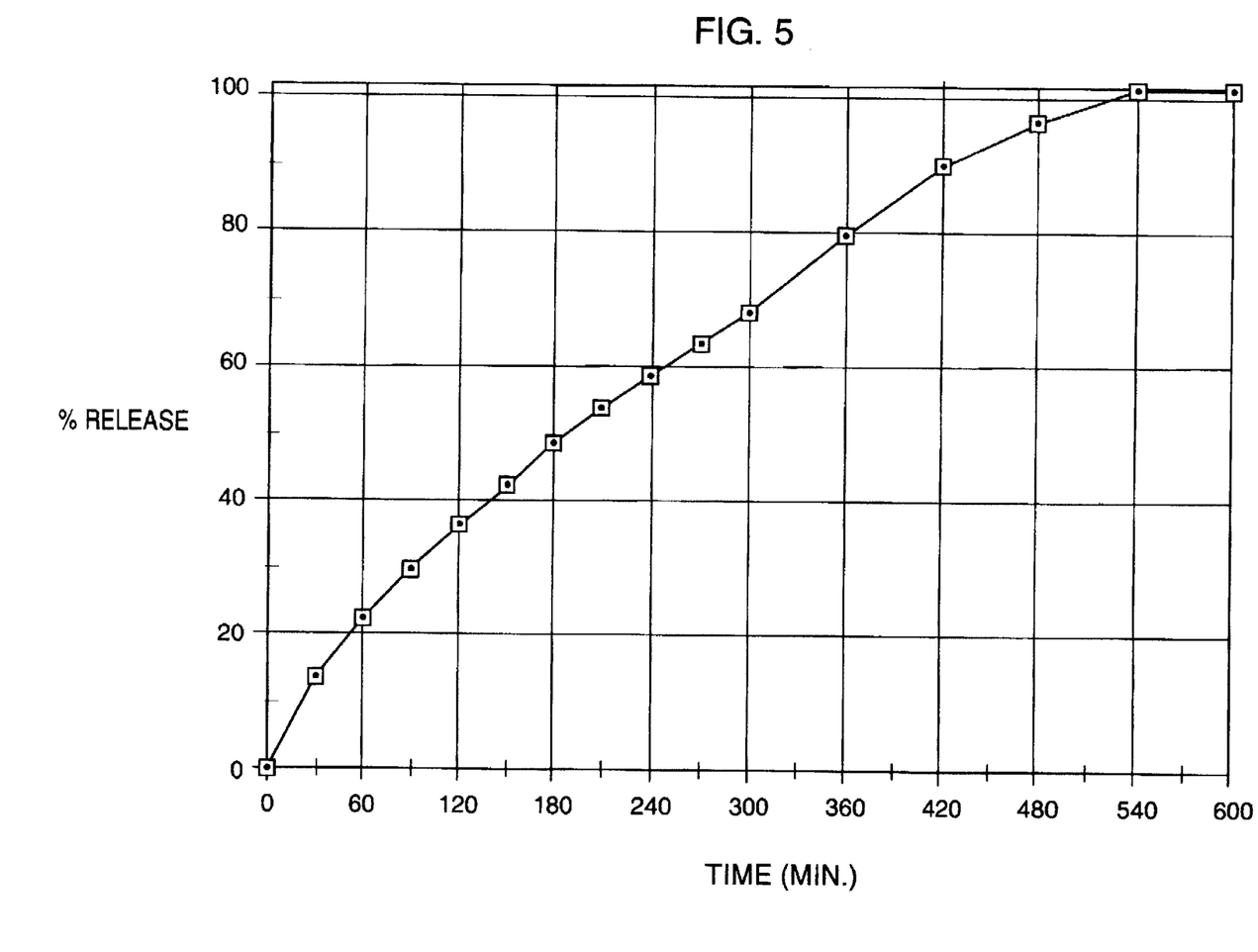

The data reported in Table I have been transferred in the FIG. 3 graph: to help in a comparison, FIGS. 4 and 5 report the graphs obtainable with the same dissolution test procedure, referred respectively only to the fast release form of 50 mg active material (that is of the trapidil itself) and only to the slow release form of 150 mg active material.

Figure 6:
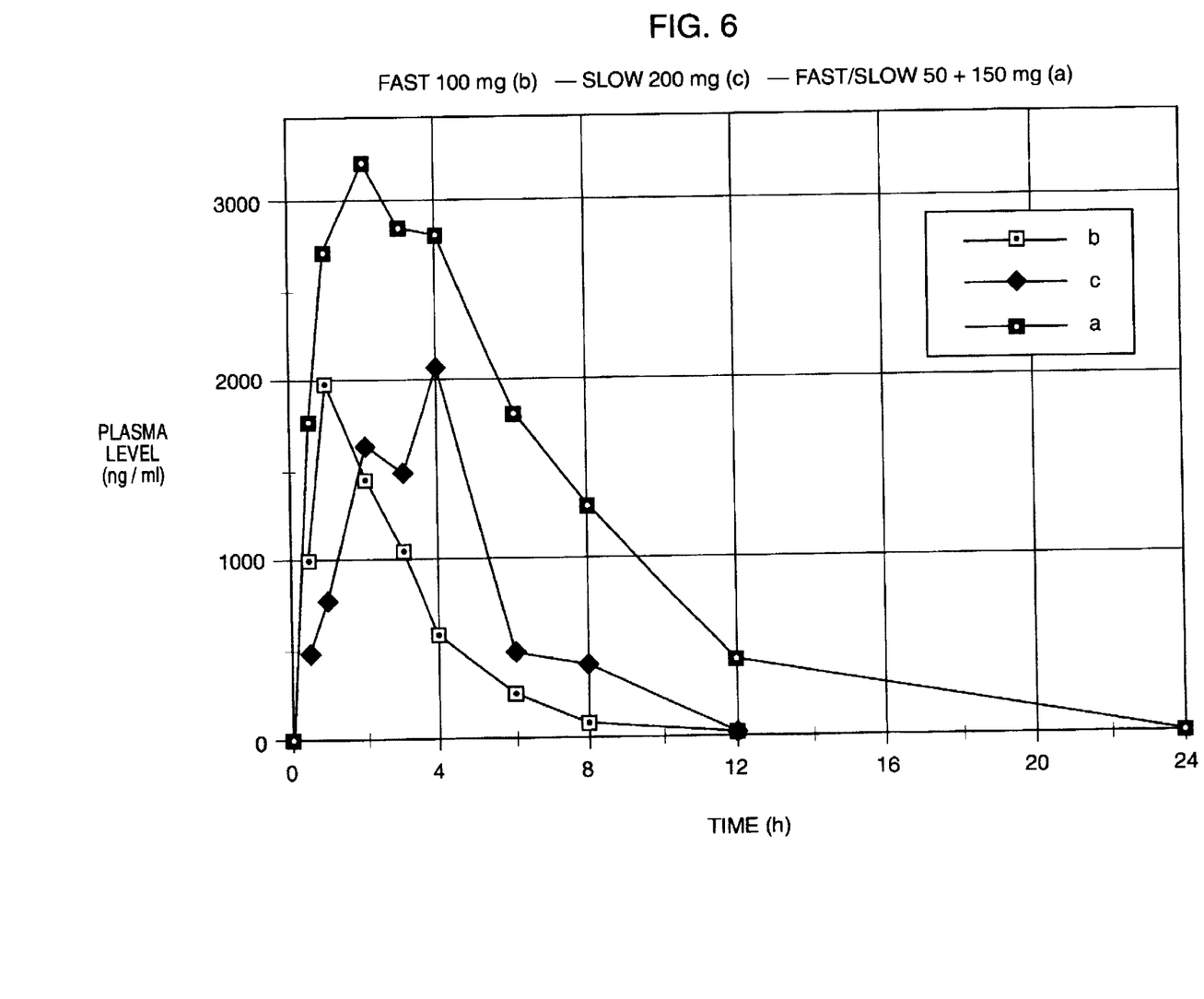
FIGS. 6 is a graph showing plasma levels as a function of time.

FIG. 6 shows the same release curves in just one graph, and it is easy to appreciate that, with the pharmaceutical form of the present invention, (curve a) an initial peak clearly higher than that attainable with the only form of retarded release is achieved, making it sufficient to add in the immediate release pharmaceutical form an active material concentration sufficient just to exceed the minimum threshold at which an immediate effect or, in other words of symptomatic treatment is attained to achieve the desired result.

In other words, from FIG. 6 it can be immediately appreciated that in the immediate release form (curve b) the 100% level of the active material release is quickly reached (within 15 minutes) and this makes to estimate that such a drug's quantity might be similarly absorbed attaining effective plasmatic concentrations. Likewise, in the case of administering the only one form of slow or retarded release (curve c), the total release occurs after a very long time, and therefore, a release level "in vivo" sufficient to produce a therapeutic effect will also be reached after a longer time.

Thus before the present invention, the therapeutical choice had to be made between adopting a symptomatic or shock therapy and a treating and maintaining therapy without, or at least with a poor symptomatic effect.

With the pharmaceutical form of the present invention comprising the two dosages of the immediate release and slow release forms respectively, as it is easy to verify from the corresponding curve (c) of FIG. 6, the release is about twice as much as that of the only slow release form, and is high enough to produce an immediate symptomatic effect.

Once this initial function is completed, the release takes place in the same way as with the slow release form, which consequently affect the release of the immediate release form.

An experimental confirmation of the previous "in vitro" tests has been obtained by carrying out the "in vivo" treatment in well being volunteers at the following dosages (and by plotting in FIG. 6 the corresponding plasmatic levels as a function of time):

(i) Fast release pharmaceutical form containing 100 mg of trapidil (curve b of FIG. 6) and (ii) Slow release pharmaceutical form containing 200 mg of trapidil (curve c of FIG. 6) and (iii) Pharmaceutical form according to the presente invention containing 200 mg of trapidil wherein the 25% of the active material dose was present as a fast release amount, and the remaining 75% was present as a slow release amount (curve a of FIG. 6).

The numerical data of the aforementioned plasmatic levels are listed in Table 1A which follows.

TABLE IA

| Time (hours) | Fast system 100 mg (ng/ml) | Slow system 200 mg (ng/ml) | Fast/Slow system 200 mg (ng/ml) |
|---|---|---|---|
| 0.5 | 1015 | 482 | 1767 |
| 1 | 1969 | 762 | 2724 |
| 2 | 1464 | 1638 | 3205 |

TABLE IA-continued

| Time (hours) | Fast system 100 mg (ng/ml) | Slow system 200 mg (ng/ml) | Fast/Slow system 200 mg (ng/ml) |
| --- | --- | --- | --- |
| 3 | 1046 | 1479 | 2855 |
| 4 | 575 | 2058 | 2813 |
| 6 | 239 | 466 | 1815 |
| 8 | 76 | 421 | 1301 |
| 12 | 11 | 14 | 440 |
| 24 | 8 | 0 | 0 |

From Table 1A and FIG. 6 it can be immediately appreciated as the pharmaceutical form of the present invention makes it possible to reach the above mentioned therapeutic advantages, namely the effect of the symptomatic treatment (obviously by adjusting in a suitable manner the dosage of the fast release portion and that of ensuring that the slow release Form will maintain its effect.

In addition the symptomatic effect is obtained with a lower dosage of active principle (obviously calculated so as to exceed the threshold over which the acute effect is attained), with the clear advantages in terms of lower toxicity or, in the case of anti-inflammatory non-steroidal drugs (FANS), lower gastrolesiveness besides a minor quantity administered to the patient.

Example 2

—Two—layered tablet containing 400 mg of 4-methoxy-N3-(3-pyrimidilmethyl)1,3-benzenedicarboxamide (compound hereinafter indicated with G619), of which one layer contains 200 mg of active material for a fast release and in a second layer there are 200 additional mg of G619 for slow release.

2-a Preparation of the granulate forming the first fast release layer, containing 200 mg of G619 as active material.

| | |
| --- | --- |
| G 619 (Farma resa batch n. 89043 | 200.00 mg |
| Maize starch | 75.00 mg |
| Mannitol | 25.00 mg |
| Polyvinylpirrolidone (10% in ethanol) | 6.25 mg |
| Carboxymethylstarch (Explotab) | 10.00 mg |
| Magnesium stearate (C. Erba) | 3.75 mg |
| Colloidal. Silica (Syloid 244) | 0.75 mg |
| Total | 320.75 mg |

2-b Preparation of the granulated used for preparing the second slow release layer wherein 200 mg of G619 are contained.

| | |
| --- | --- |
| G 619 (Farma resa batch N. 89043) | 200.0 mg |
| Mannitol (C. Erba, Milan, I) | 50.0 mg |
| Hydroxypropylmethylcellulose (Methocel K 4 M, Colorcon, Orpington UK) | 30.0 mg |
| Hydroxypropylmethylcellulose (Methocel E 5, Colorcon, Orpington UK) | 30.0 mg |
| Polyvinylpirrolidone (Plasdone K29–32, Gaf Corp, Wayne NY USA) | 13.0 mg |
| Magnesium Stearate (C. Erba, Milan, I) | 2.5 mg |
| Colloidal Silica (Syloid 244, Grace GmbH, Worms, D) | 0.5 mg |
| Total | 326.0 mg |

Both these layers are prepared as per Example 1.

2-c Preparation of the finished systems (by compression)

The same rotative compression machine, equipped with oblong (capsule-type) punches of 19×9 mm, as described in Example 1, is used to prepare the tablets. The first loading hopper is filled with the granulate described at point 2-a (granulate A), while the second one is filled with the granulate described in 2-b (granulate B). The first loading station is adjusted in order to provide layers of 320,75 mg of granulate (equal to 200 mg active material), while the second loading station is adjusted so as to provide an amount of granulate B (with slow active material release) of 326.0 mg equal to 200 mg active material.

By operating as previously illustrated, two-layered tablets with an average weight of 646,75 mg, totally containing 400 mg of G619, are produced.

Said finished systems are subjected to the dissolution test as hereunder specified. 2-d Dissolution test To evaluate the releasing features of the finished (two-layered) systems, the 2 paddle apparatus (as per USPXXII) is used, operating at 100 r.p.m. and with 1000 ml at 37° C. of deionized water used as a dissolution fluid. The active material release is monitored by U.V. spectrophotometric determination at 251 nm, with an automatic system of sampling and dosage, as well as with an automatic data processing program (Spectracomp 602, Advanced Products Milano).

The results of the tests carried out are listed in Table II.

TABLE II

| Time (min) | % Released G619 |
| --- | --- |
| 15 | 53,0 |
| 30 | 58,5 |
| 60 | 65,0 |
| 120 | 78,2 |
| 180 | 90,3 |
| 240 | 98,5 |
| 360 | 100,4 |

It is evident that of the 400 mg of the carried active material, 50% (first amount) is fast released, in 15 minutes, whereas the second amount is released in about 4–6 hours.

Example 3

Two layer tablet containing 800 mg of ibuprofen, one fast release layer containing 250 mg of active principle and the other slow release layer containing 550 mg of ibuprofen.

3-a Preparation of the granulate forming the first fast release layer containing as the active principle 250 mg of ibuprofen.

| | |
| --- | --- |
| Ibuprofen (CFM B. 2235/18/87) | 250.00 mg |
| Maize starch (USP grade, C. Erba, Milan, I) | 74.63 mg |
| Dye (Nacarat Red E 120) | 0.25 mg |
| Methylcellulose (BDH, Poole, UK) | 1.25 mg |
| Sodium laurylsulfate (C. Erba, Milan, I) | 0.75 mg |
| Carboxymethylstarch (USP grade) | 18.75 mg |
| Crosslinked polyvinylpyrrolidone (Polyplasdone XL, ISP, Wayne, US) | 7.50 mg |
| Magnesium stearate (C. Erba, Milan, I) | 3.37 mg |
| Total | 356.50 mg |

The manufacturing process comprises the preparation of a granulate obtained by admixing, in a sigma mixer (Erweka model type K 5, Frankfuert a.M., D) the proper amounts of active principle and 50 mg of maize starch; the homogeneous powder mixture is wetted with a 1.3% (w/v) aqueous solution of methylcellulose in which the sodium laurylsulfate and the dye have been previously dissolved; the homogeneously moistened mass is forced through a 25 mesh (710 um) grid leading to a regular granulate which is dried in an air circulation oven at 40°–45° C. The granulate, after drying to constant weight, is placed into a powder mixer (Turbula mod.T2A, Bachofen, Basel, CH), added with the crosslinked polyvinylpyrrolidone, the remaining 24.63 mg of maize starch and the carboxymethylstarch and admixed for 20 minutes. Then the magnesium stearate is added and the admixing is continued for further 20 minutes. The granulate, lubricated and analyzed for the content of active principle, is subjected to the hereinafter described compression phase.

3-b Preparation of the granulate used for the second slow release layer containing 550 mg of ibuprofen.

| | |
|---|---|
| Ibuprofen (CFM B. 2235/18/87) | 550.0 mg |
| Hydroxypropylmethylcellulose (Methocel K4K Colorcon, Orpington UK) | 183.3 mg |
| Mannitol (C. Erba, Milan, I) | 110.0 mg |
| Polyvinylpyrrolidone (Plasdone K 29 ISP, Wayne, NY USA) | 18.3 mg |
| Talc (C. Erba, Milan, I) | 16.5 mg |
| Magnesium stearate (C. Erba, Milan, I) | 3.7 mg |
| Colloidal silica (Syloid 244, Grace GmbH, Worms D) | 0.9 mg |
| Total | 882.7 mg |

A granulate is preparaed by admixing in a sigma nixer (Erweka model type K5) the proper amounts of ibuprofen, mannitol and hydroxypropylmethylcellulose (Methocel K4M, apparent viscosity 4,000 cP); the homogeneous powder mixture is wetted with a 10% (w/v) alcoholic solution of polyvinylpyrrolidone and the homogeneously wetted mass is forced through a 25 mesh grid leading to a regular granulate which is dried in an air circulation oven at 40°–45° C. The granulate, dried to constant weight, is placed in a powder mixer (Turbula model T2A) and added with talc, magnesium stearate and colloidal silica, and admixed for 20 minutes. The granulate is then compressed as hereinafter described.

3-c Preparation of the finished systems (by compression)

For the preparation of the tablets the same rotating compression machine and the same operating conditions as in the previous examples are used, so as to obtain two layer tablets.

The resulting tablets have an avenge weight of 1239.2 mg containing on the whole 800 mg of ibuprofen, which are subjected to the dissolution test as hereinafter specified.

3-d Dissolution test

In order to assess the realeasing behaviour of the tablets the 2 paddle apparatus is used (USP XXII) adjusted for a vessel of 5 liters capacity in order to maintaining the sink conditions, the test being carried out at 100 r.p.m. and using as the dissolution fluid 5 l of simulated intestinal fluid (USP XXII), without enzymes at 37° C. The release of the active principle is monitored by U.V. spectrophotometric measurement at 223 nm, using an automatic sampling and reading system (Spectracomp 602 of Advanced Products, Milano, I).

The results of the test are reported in the following table III

TABLE III

| time (h) | Released % (total) |
|---|---|
| 0.5 | 31.3 |
| 2 | 37.0 |

TABLE III-continued

| time (h) | Released % (total) |
|---|---|
| 4 | 42.9 |
| 8 | 52.9 |
| 12 | 66.2 |
| 16 | 78.5 |
| 20 | 88.0 |
| 24 | 99.1 |

It is thus seen that from the tablets the fast release of the first amount of drug (about 31% of the total) is obtained within 30 minutes, whereas in the second phase, definitely differentiated from the first one, the drug is released under controlled rate in about 24 hours.

The foregoing examples refer to pharmaceutical forms containing only one active material divided within two layers.

It is understood that is also possible and foreseen within the scope of the present invention to produce, with the above mentioned procedures, three-layered pharmaceutical forms, that is with delayed release of the same active material but adjusted at different rates from one layer to another.

Similarly, the third layer might instead include another active material for supplementing, at a certain point of the treatment, the therapeutic effect of the first active material, already released in fast and/or slow released form as well.

So far the realisation of the aforementioned pharmaceutical forms is concerned, these are made with the galenical technics already cited, and by employing the adjuvants and carriers well known by themselves in the technical field.

It should be finally noted that the previous list of the active materials which can be used in the pharmaceutical forms of the present invention is not intended as a limit since, as it is evident, the invention is extended to all the active materials, for which is foreseen or foreseable either the fast release administration for a systemic therapeutic effect or the slow release administration for a treatment of maintaining or prolonging the main therapeutical effect.

We claim:
1. A solid pharmaceutical composition for oral administration, comprising:
   at least one first layer consisting essentially of a first active material and a disintegrating or superdisintegrating compound which is a cross-linked polyvinylpyrrolidone, sodium carboxy methylcellulose, carboxymethyl starch, potassium methacrylate—divinylbenzene copolymer, a polyvinylalcohol, a starch, a microcrystalline cellulose, a dextrin, beta cyclodextrin, and mixtures thereof; and
   at least one second layer located on said first layer containing a portion of said first active material or a second active material and an excipient or adjuvant selected from the group consisting of hydroxypropylmethylcellulose of molecular weight 1,000 to 4,000,000, hydroxypropylcellulose of molecular weight from 2,000 to 2,000,000, a carboxyvinylpolymer, a polyvinylalcohol, a glucan, a scleroglucan, a mannan, a xanthan, alginic acid, methylcellulose and a polymethylcellulose;
   said active material in said first layer being released upon administration to a host at a rate faster than the rate of release of said active material in said second layer.

2. A pharmaceutical composition according to claim 1, wherein said disintegrating or superdistintegrating compound is present in an amount of 10 to 90% by weight of said first layer.

3. A pharmaceutical composition according to claim 2, wherein said disintegrating or superdisintegrating compound is present in an mount of 20 to 70% by weight of said first layer.

4. A pharmaceutical composition according to claim 1, wherein said said first layer further comprises an adjuvant selected from the group consisting of starch, pregelled starch, calcium phosphate, mannitol, lactose, sucrose, glucose, sorbitol and microcrystalline cellalose, a binding agent, a lubricant and an antiadhering compound.

5. A pharmaceutical composition according to claim 4, wherein said binding agent is selected from the group consisting of gelatin, polyvinylpyrrolidone, methyl cellalose, starch water, ethylcellulose, gum arabic and tragacanth gum.

6. A pharmaceutical composition according to claim 4, wherein said lubricants and antiadhering compounds are selected from the group consisting of magnesium stearate, stearic acid, colloidal silica, glyceryl monostearate, a polyoxyethyleneglycol of 400 to 50000 number average molecular weight, hydrogenated castor oil, waxes and a glyceride.

7. A pharmaceutical composition according to claim 1, wherein said first layer includes an effervescent agent capable of causing rapid disintegration of said first layer when said composition comes into contact with an aqueous environment.

8. A pharmaceutical composition according to claim 7, wherein said aqueous environment is gastric juice.

9. A pharmaceutical composition according to claim 7 wherein said first layer includes a compound that can produce effervescence in an acid environment selected from the group consisting of alkali metal carbonates, alkaline-earth metal carbonates, sodium bicarbonate and glycine sodium carbonate.

10. A pharmaceutical composition according to claim 7, where said first layer includes a compound that can produce effervescence and disintegration of said first layer independently of pH selected from the group consisting of citric add, tartaric acid and fumaric add.

11. A pharmaceutical composition according to claim 7, wherein said effervescent agent capable of producing effervescence is present in an amount of 3 to 40% by weight of said first layer.

12. A pharmaceutical composition according to claims 1, and further comprising a second and a third layer including a same or different active material together with a disintegrating or superdisintegrating compound which is a cross-linked polyvinylpyrrolidone, sodium carboxy methylcellulose, carboxymethyl starch, potassium methacrylate—divinylbenzene copolymer, a polyvinylalcohol, a starch, a microcrystalline cellulose, a dextrin, beta cyclodextrin, and mixtures thereof, and excipients and adjuvants.

13. A pharmaceutical composition according to claim 12, wherein said disintegrating or superdisintegrating compound in said second and third layer is present in each layer in an amount of 5 to 90% by weight of the said layer.

14. A pharmaceutical composition according to claim 1, wherein said adjuvant contained in said at least one second layer is selected from the group consisting of polyvinylpyrrolidone, methylcellulose, starch water, ethylcellulose, arabic gum and tragacanth gum.

15. A pharmaceutical composition according to claim 1, wherein said adjuvant of said at least one second layer is selected from the group consisting of glyceryl monostearate, semi-synthetic glycerides, glyceryl palmitostearate, glyceryl behenate, microcrystalline cellulose, sodium carboxymethylcellulose, magnesium stearate, stearic acid, sodium stearate, talc, sodium benzoate, boric acid and colloidal silica.

16. A pharmaceutical composition according to claim 1, wherein said adjuvant of said at least one second layer is selected from the group consisting of hydrogenated castor oil, fatty acids, waxes, glycerides and polyoxyethyleneglycol with a molecular weight of from 400 to 60,000.

17. A pharmaceutical composition according to claim 1, wherein said active material is selected from the group consisting of steroidol anti-inflammatories non-steroidal anti-inflammatories (NSAID1), sleeping substances, tranquilizers, active substances for preventing anginous and hypertensive attacks, antihistamines and antiasthmatic drugs, and combinations thereof.

18. A pharmaceutical composition according to claim 17, wherein said anti-inflammatory is selected from the group consisting of diclofenac sodium, indomethacin, ibuprofen, ibuprofen lysine salt, ketoprofen, diflunisal, piroxicam, naproxen and flurbiprofen.

19. A pharmaceutical composition according to claim 17, wherein said sleeping substance or tranquilizer is selected from the group consisting of diazepam, nitrazepam, fluorozepam, oxazepam and chlorodiazepoxide.

20. A pharmaceutical composition according to claim 17, wherein said antianginous and antihypertensive active material is selected from the group consisting of diltiazem, trapidil, verapamil, urapidil and benziodarone dipyridamole.

21. A pharmaceutical composition according to claim 17, wherein said antihistaminic or antiasthmatic material is selected from the group consisting of ephedrine, terfenadine, theophylline, chloropheniramine and termutiline.

22. A pharmaceutical composition according to claim 1, wherein said first layer has a thickness from 0.5 to 5 mm and contains from 1 to 90% by weight of active material.

23. A pharmaceutical composition according to claim 1, wherein said second layer has a thickness of from 0.1 to 6.0 mm and contains from 1 to 90% by weight of active material and from 10 to 90% by weight of said excipient or adjuvant.

24. A pharmaceutical composition according to claim 1, wherein said second layer contains a portion of the same active material as present in said first layer.

25. A pharmaceutical composition according to claim 1, wherein an active material different from that present in said first layer is present in said second layer.

26. A pharmaceutical composition according to claim 1, wherein a third layer is present and contains an active material and an adjuvant as defined in claim 1.

* * * * *